United States Patent [19]

McEntee

[11] Patent Number: 5,064,086
[45] Date of Patent: Nov. 12, 1991

[54] CONTAINER LID

[76] Inventor: James E. McEntee, 1250 Lochshyre Way, Lawrenceville, Ga. 30245

[21] Appl. No.: 648,737
[22] Filed: Jan. 31, 1991
[51] Int. Cl.5 ............................................. B65D 51/18
[52] U.S. Cl. .................................... 220/253; 220/256
[58] Field of Search ................ 220/253, 256, 262, 336

[56] References Cited

U.S. PATENT DOCUMENTS

| | | |
|---|---|---|
| 1,489 | 10/1840 | Lowell . |
| 219,399 | 9/1879 | Henkel . |
| 311,415 | 1/1885 | Cleveland . |
| 1,160,974 | 11/1915 | Clyne . |
| 1,449,204 | 3/1923 | Viehmann . |
| 2,538,946 | 1/1951 | Nyden et al. ................... 220/336 X |
| 2,627,992 | 2/1953 | Kurz . |
| 3,860,111 | 1/1975 | Thompson ...................... 220/253 X |
| 4,036,387 | 7/1977 | Feaster . |
| 4,141,461 | 2/1979 | LaChance ........................... 220/253 |
| 4,203,527 | 5/1980 | LaChance, Sr. .................... 220/253 |
| 4,548,331 | 10/1985 | Montgomery . |
| 4,550,850 | 11/1985 | Smith et al. . |
| 4,832,219 | 5/1989 | Nycz ................................. 220/253 X |
| 4,940,157 | 7/1990 | Inagaki .............................. 220/254 |

FOREIGN PATENT DOCUMENTS 1185853  2/1959  France ................................ 220/253

Primary Examiner—Stephen Marcus
Assistant Examiner—Nova Stucker
Attorney, Agent, or Firm—James A. Hinkle

[57] ABSTRACT

A container lid, especially useful in the pharmaceutical testing industry, having a pair of overlapping lid elements which are rotatable with respect to one another. The lid elements have matching apertures which allow the insertion of testing apparatus into the container covered by the lid without the necessity of removing the lid. The rotatable elements may be positioned tightly around the testing apparatus to reduce the possibility of evaporative loss and of contamination of the testing medium.

6 Claims, 3 Drawing Sheets

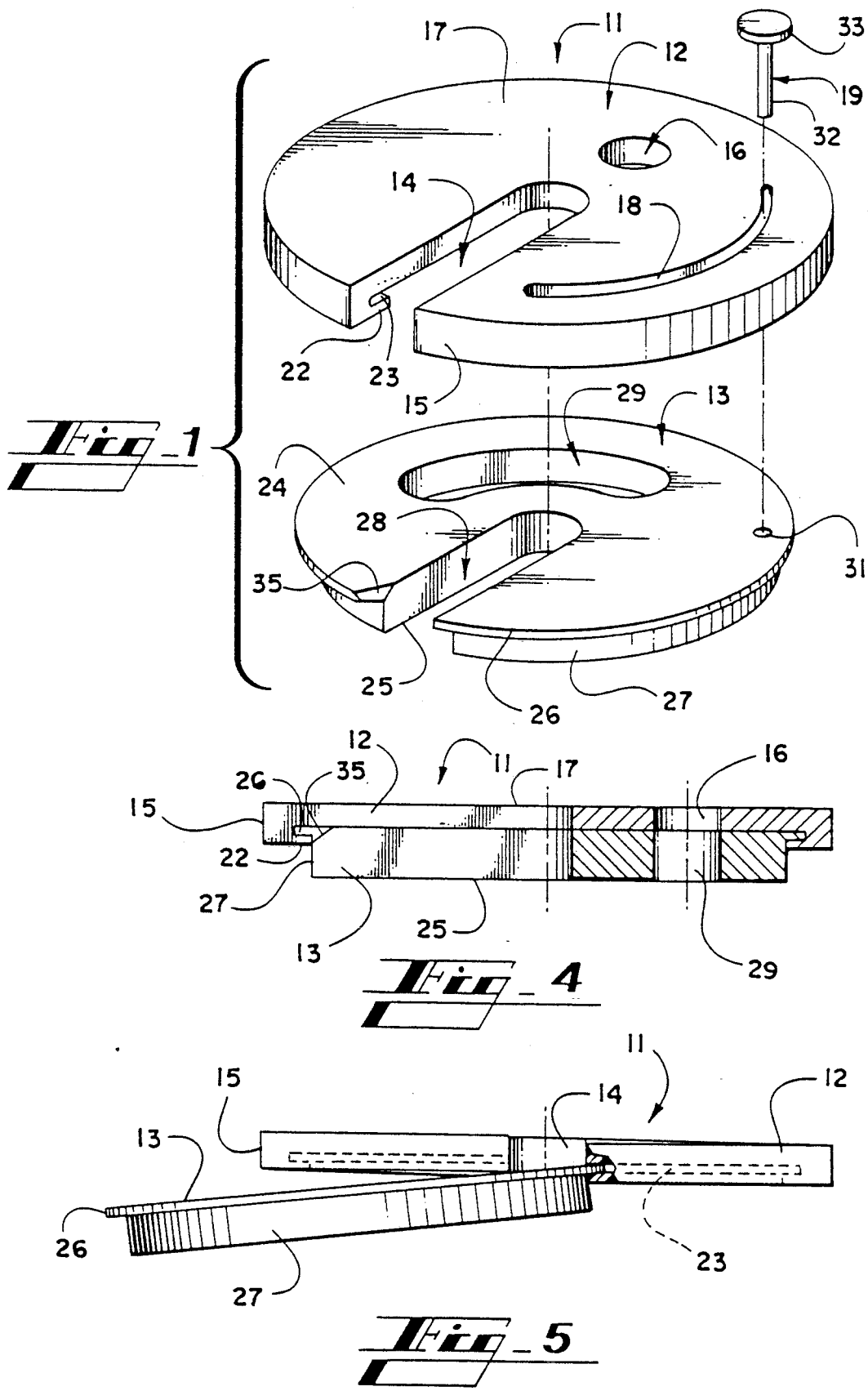

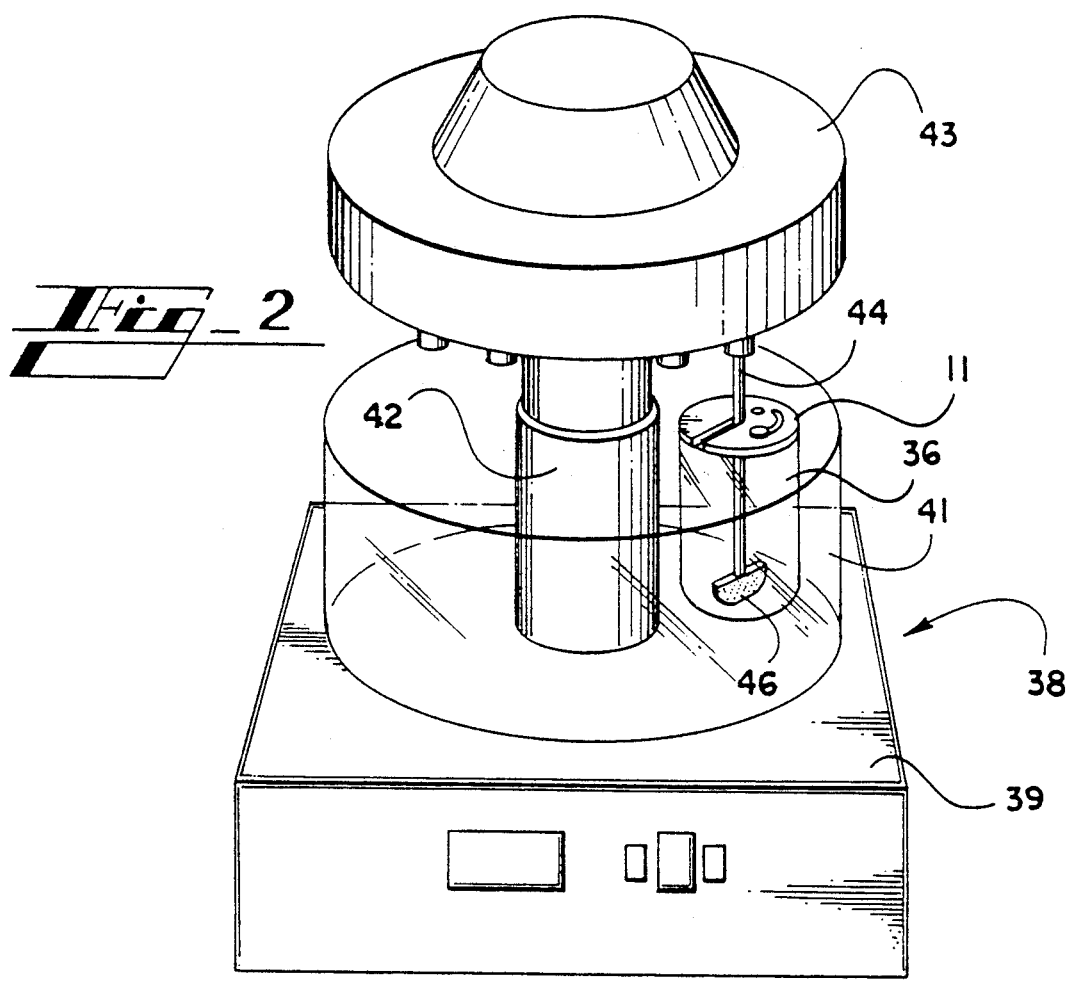
Fig_2
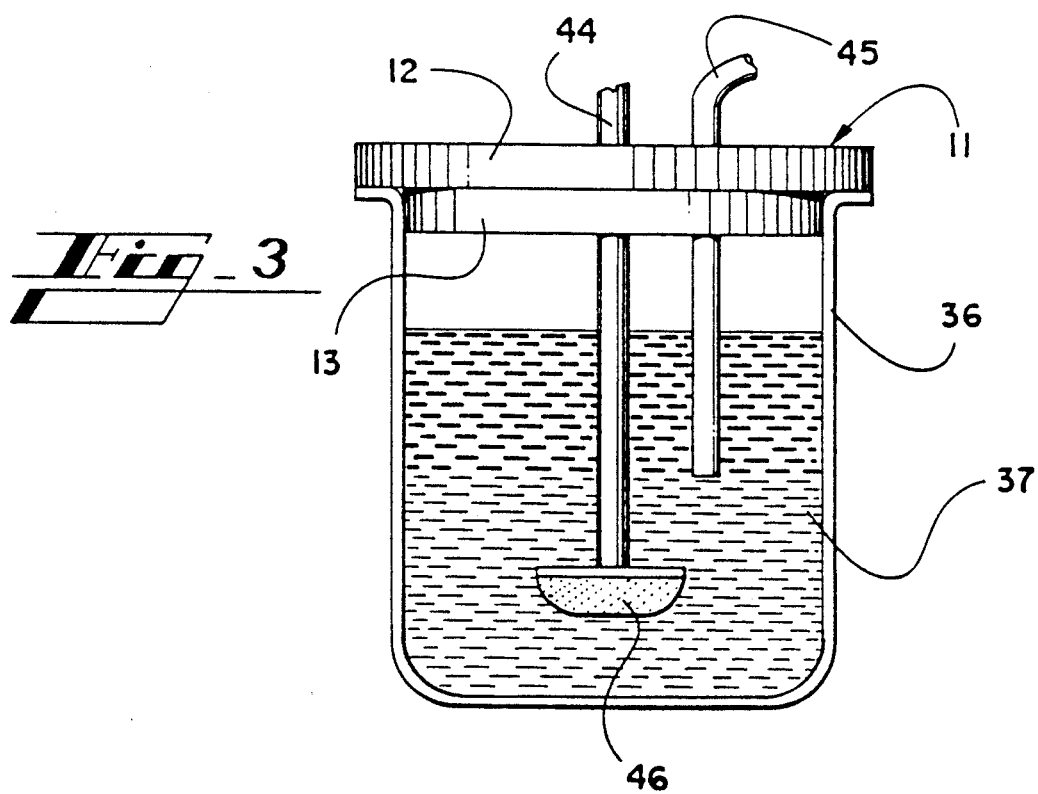
Fig_3

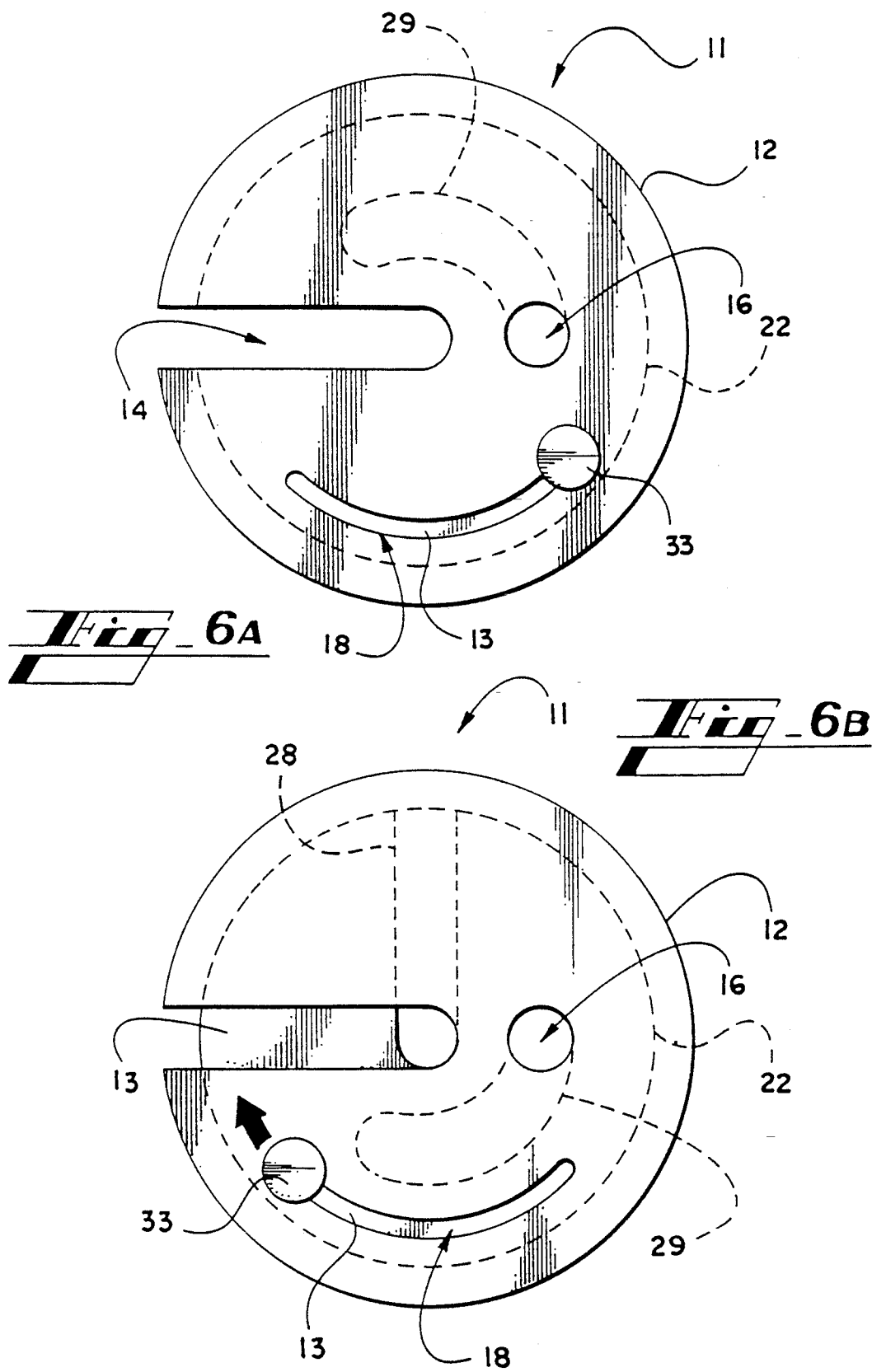

CONTAINER LID

BACKGROUND OF THE INVENTION

I. Field of the Invention

The present invention relates generally to the field of container lids, and more particularly, to a lid for use in an environment wherein a vessel is to be covered to minimize evaporation of the fluid therefrom and yet a lid that has openings therein, which openings are capable of being utilized to gain admittance to the interior of the vessel without the lid being removed therefrom.

II. Description of the Prior Art

In the field of pharmaceutical testing, the instruments and mechanisms which are utilized to test certain pharmaceutical compounds require extreme accuracy and repeatability of the tests. Such testing equipment is well known in the prior art and is widely available and utilized. In certain test procedures, specifically in dissolution tests wherein timed release capsules and tablets are tested, it is necessary to measure the dissolution of such tablets and capsules over an extended period time while maintaining the level of solution and the temperature thereof within precise limits.

The vessels which typically are utilized have test instruments placed therein and means to maintain a constant environment for the testing solution. However, there is quite a problem in maintaining the level of solution over an extended period of time, and yet being able to monitor the solution and to take samples therefrom at convenient times. Typically if the solution container is open to the ambient atmosphere then there is considerable evaporation from the solution thereby giving incorrect results from the test. In addition, open containers make it harder to maintain a consistent temperature level of the solution.

In the past, certain inert lids have been utilized to cover the containers, but the lids must be preformed with slots and holes therein by which testing instruments and sampling devices may be placed to effect the monitoring of the solution. Obviously, with a fixed lid having fixed apertures therein, it is difficult to effect testing procedures by inserting and removing stirrers, pipettes, thermometers and other monitoring devices without removing the lid entirely or without compromising the results of the solution by evaporative loss or lack of temperature control. The prior art devices have proven to be less than satisfactory in actual use.

SUMMARY OF THE INVENTION

In accordance with the present invention it is contemplated to provide a container lid having a plurality of overlapping matingly engaged circular lid members mounted in axial alignment which are designed to cover the solution containing vessel in a pharmaceutical test environment, and yet allow the selective insertion and removal of test equipment without removing the lid from the vessel and without compromising the solution therein.

It is, therefore, an object of the invention to provide a novel and unique container lid which is suitable for pharmaceutical testing.

Another object of the invention is the provision of a container lid having multiple overlapping lid members matingly engaged so that the lid members may be rotated relative to one another to effect opening and closure of access apertures within the various members of the lid.

Yet another object of the invention is the provision of an easily manufactured, relatively inexpensive container lid for utilization in a test environment which allows the insertion and removal of various testing equipment through the lid without removing the lid from the vessel containing the test medium, and which lid will retain the tested medium under desired controlled conditions.

Other objects, advantages and capabilities of the invention will become apparent from the following description, taken in conjunction with the accompanying drawings, showing only a preferred embodiment of the invention.

BRIEF DESCRIPTION OF THE DRAWINGS

FIG. 1 is an exploded perspective view of the container lid elements of the present invention;

FIG. 2 is a perspective view of a typical testing apparatus with which the present invention is designed for use;

FIG. 3 is a partial vertical section view of a solution containing vessel with which the present invention is used;

FIG. 4 is a partial vertical section view of the container lid;

FIG. 5 is a vertical section view with a portion of the lid broken away for clarity showing the manner in which the lid elements are assembled;

FIG. 6A is a top plan view of the container lid in an open condition; and

FIG. 6B is a top plan view of the container lid in a closed position.

DESCRIPTION OF THE PREFERRED EMBODIMENT

Referring to the drawings wherein like reference numerals designate corresponding parts throughout the several figures, the container lid is generally indicated by the numeral 11. The lid 11 generally comprises a two-piece lid structure having an upper lid element 12 and a lower lid element 13 which are co-extensive and mated one to the other as more fully seen in FIG. 4.

The upper lid element 12 is of circular design and may be made in a plurality of sizes to fit various vessels which are commonly used in pharmaceutical testing. The upper lid element 12 has a radially disposed upper access slot 14 extending from edge 15 to a point encompassing the axial center of the element 12. The slot 14 is of such size as to permit the placement of the container lid 11 about typical testing apparatus in the intended environment, and to receive such apparatus within the slot. A circular access aperture 16 is placed through the upper surface 17 of lid element 12 to provide an additional access opening to accept testing equipment as may be desired. Disposed in an arc within the upper surface 17, near the edge 15, is a slot 18 which permits the lower lid control shaft 19 sufficient room for movement at desired times. To be most effective, the slot 18 should have an arcuate angle of approximately 90 degrees. The planar lower surface 21 of the lid element 12 terminates in a depending edge 15 which forms a reentrant lip 22, thereby forming a slot 23 between the lower surface 21 and the reentrant lip 22. The re-entrant lip 22 and the slot 23 continue around the circumference of the upper lid element 12 with the exception of the gap formed by the access slot 14.

A lower lid element 13, which is designed to be matingly engaged with upper lid element 12 as more fully shown in FIG. 4, comprises a round disc having an upper surface 24 and a lower surface 25 wherein the upper surface terminates at the lower lid engagement lip 26, and the lower surface terminates at the recessed sidewall 27. The engagement lip 26 thereby defines a structure which is of equivalent dimensions to the slot 23 formed in the lower surface 21 of the upper lid element 12 so that the engagement lip 26 will matingly engage with the slot 23 to maintain lid elements 12 and 13 in a co-extensive juxtaposed manner.

In a similar manner to upper lid 12, the lower lid 13 has a radially disposed access slot 28 extending from the engagement lip 26 to a point encompassing the axial center of the element 13. The preferred form of slot 28 requires the same configuration and size of slot 14 of the upper lid element so that when the lid elements are fabricated and the slots are aligned, the slot openings will be matching.

Projecting through the lower lid element 13 is an elongated access slot 29 disposed in an arc parallel to the engagement lip 26 having an arcuate angle of approximately 90 degrees. Also near the engagement lip 26 is a stem aperture 31 which does not fully project through the entire lid element 13. The purpose of aperture 31 is to accept the stem 32 of the lower lid control shaft 19. As is evident from FIG. 1, once the lid elements 12 and 13 are matingly engaged, the control shaft 19 is placed through the arcuate slot 18 of upper lid element 12 and thence into the aperture 31 to be retained so that upon desired times an operator utilizing the lid may grasp actuator 33, thereby circularly moving lower lid element 13 with respect to upper lid element 12.

An interesting aspect of the present invention is that the upper and lower lid elements 12 and 13, respectively, are manufactured separately and must be assembled after such separate manufacturing is completed. However, because of the shape and rigidity of the separate elements, the method by which they must be assembled is rather unique, as depicted by FIG. 5. To assemble elements 12 and 13, the assembly person will typically hold element 12 in one hand and press down upon the upper surface 17 at the outer edge of access slot 14, thereby deforming the lid slightly in a direction toward the lower surface 21 thereof. The deformation of the element during assembly is shown by numeral 34. Once the lid element 12 has been deformed in the described manner, the operator then takes lower lid element 13 with the other hand and engages the lower lid engagement lip 26 at the area of the beveled corner 35 with slot 23. Once the engagement lip 26 is started into slot 23 the assembly person would then counterrotate the lid elements thereby causing engagement lip 26 to fully engage slot 23 throughout the entire circumference of upper lid element 12 which, in effect, screws the two lid elements together in the final assembled arrangement. Once the two lid elements are assembled, the assembly person would then place control shaft 19 through the arcuate slot 18 into aperture 31 thereby providing a means to the ultimate operator for moving the respective lid elements relative to one another at desired times.

In FIG. 6A the container lid 11 is shown in its open position in such a fashion that the lid can be placed upon the beaker vessel 36 to enclose the solution 37 therein. FIGS. 2 and 3 show one proposed use of the present invention. In the pharmaceutical industry it is typical to utilize a dissolution stirring machine 38, as depicted in FIG. 2, comprising a housing 39 and a liquid container 41 which maintains constant temperature around the beaker 36. The typical stirring machine will have a support housing 42 connected to a motive means cover 43. In the embodiment shown, the motive means cover 43 controls a multiple array of stirring elements 44 which are designed to hold a possible capsule or tablet whose rate of dissolution is to be monitored. As shown in FIG. 3, an instrument 45 may be inserted through the lid 11 for such purposes as temperature monitoring, solution removal or solution monitoring.

In actual use it is typical to place the beaker 36 in its intended position on the dissolution stirring machine 38, and then place the stirring element 44 therein and into the solution 37. The pharmaceutical to be tested would normally be placed within the lower end basket 46 to be revolved within the solution at a constant stirring rate. To seal off the top of the beaker 36, the testing personnel would place the lid 11 around the stirring element 44 and seat it as shown in FIG. 3. To close off the openings and prevent evaporation or excessive temperature loss, the operator would grasp actuator 33 and rotate the lids relative to one another thereby closing the access slots 14 and 28, leaving only a central hole in the lid to encompass the stirring element 44. Because of the arcuate elongated access aperture 29, the access aperture 16 of the upper lid element 12 will always have available access to the solution 37 for the insertion of a testing implement at any time during the test.

As can be seen, the present invention provides the maximum coverage of the dissolution vessel thereby minimizing the common problem of solution evaporation during the testing of extended release tablets, and the unique design allows the quick insertion of testing implements when monitoring is desired. With the present construction the lid can be placed on or removed from the beaker without removing instrumentation connected therewith, and once in place on the beaker additional test implements can be placed into solution and redrawn therefrom without removing the lid.

Various modifications may be made of the invention without departing from the scope thereof, and it is desired, therefore, that only such limitations shall be placed thereupon as are imposed by the prior art and which are set forth in the appended claims.

What is claimed is:

1. A multi-piece container lid comprising:
   a circular upper lid element and a circular lower lid element each having a central axis,
   the lid elements each having a planar upper surface and a planar lower surface and wherein the lid elements are mounted in overlapping juxtaposed axial alignment with one another,
   the lower lid element being matingly engaged with the upper lid element and being mounted thereto to effect relative circumferential movement between the respective lid elements,
   means mounted in cooperative engagement between the lower lid element and the upper lid element to effect relative movement between the lid elements,
   the upper element having a peripheral down turned edge, the downturned edge having a re-entrant lip projecting inwardly toward the center of the upper lid element and wherein the lip extends approximately parallel to the lower surface of the upper lid element, the upper lid element having a slot formed through the peripheral downturned edge and the re-entrant lip, and extending inwardly toward the axis of the upper lid element.

2. A multi-piece container lid as claimed in claim 1 wherein the lower lid element has a peripheral edge located inwardly of the re-entrant lip of the upper lid element.

3. A multi-piece container lid as claimed in claim 2 comprising an outwardly projecting engagement lip forming an extension of the upper planar surface of the lower lid element, the engagement lip having a configuration to enable the engagement lip to fit within the slot of the upper lid element.

4. A multi-piece container lid as claimed in claim 3 wherein each of the lid elements have a slot radially extending from the axis of the respective lid element to the farthest peripheral edge thereof.

5. A multi-piece container lid as claimed in claim 4 wherein the upper lid element has an arcuate slot therein, the relative movement means projecting through the upper lid element arcuate slot and being fixed to the lower lid element.

6. A multi-piece container lid as claimed in claim 4 wherein one of the lid elements has an aperture therein located between the axis of the lid element and the farthest peripheral edge thereof, the other lid element having an arcuate slot located between the axis of the lid element and the farthest peripheral edge thereof, the aperture and the arcuate slot being juxtaposed with one another.

* * * * *